United States Patent [19]

Haga

[11] Patent Number: 4,845,299

[45] Date of Patent: Jul. 4, 1989

[54] METHOD FOR THE PREPARATION OF BIS(HYDROXYPHENYL) SULFIDES

[75] Inventor: Masami Haga, Tokuyama, Japan

[73] Assignee: Idemitsu Petrochemical Company, Ltd., Tokyo, Japan

[21] Appl. No.: 177,620

[22] Filed: Apr. 5, 1988

[30] Foreign Application Priority Data

Apr. 13, 1987 [JP] Japan .................. 62-90140

[51] Int. Cl.$^4$ ........................................... C07C 148/02
[52] U.S. Cl. .................................... 568/23; 568/48
[58] Field of Search ........................... 568/23, 48

[56] References Cited

U.S. PATENT DOCUMENTS 3,057,926 10/1962 Coffield ............................ 568/48
3,060,121 10/1962 Orloff ............................... 568/48
3,726,928 4/1973 Fuchsman ....................... 568/48

FOREIGN PATENT DOCUMENTS 249699 9/1987 Fed. Rep. of Germany ........ 568/48
5024233 3/1974 Japan .

Primary Examiner—Mary E. Ceperley
Attorney, Agent, or Firm—Wyatt, Gerber, Burke and Badie

[57] ABSTRACT

The bis(hydroxyphenyl) sulfides mixture prepared according to the inventive method is advantageous in respect of the increased proportion of 4-mercaptophenol relative to less useful 2-mercaptophenol in the product obtained by the reductive decomposition of the mixture. The inventive method is characterized by performing the reaction of phenol and sulfur chloride in a specific solvent which is an ethylene glycol monoalkyl ether compound such as ethylene glycol monomethyl ether, triethylene glycol monoethyl ether and the like.

8 Claims, No Drawings

METHOD FOR THE PREPARATION OF BIS(HYDROXYPHENYL) SULFIDES

BACKGROUND OF THE INVENTION

The present invention relates to a method for the preparation of a bis(hydroxyphenyl)sulfides as an intermediates for the preparation of 4-mercaptophenol which in turn is a starting material for the synthetic preparation of, for example, 1,7-di(4-hydroxyphenylthio)-3,5-dioxaheptane as a color developing agent in heat-sensitive recording paper. More particularly, the invention relates to an efficient method for the preparation of a bis(hydroxyphenyl)sulfides capable of being reductively decomposed into a mixture of mercaptophenols containing 4-mercaptophenol in a greatly increased proportion relative to less useful 2-mercaptophenol by the reaction of phenol and sulfur chloride ($S_2Cl_2$).

As is mentioned above, 4-mercaptophenol is a useful compound as a starting material of various sulfur-containing organic compounds. For example, 1,7-di(4-hydroxyphenylthio)-3,5-dioxaheptane as a color developing agent in heat-sensitive recording paper is synthesized by reacting 4-mercaptophenol with bis(2-chloroethoxy)methane while 4-mercaptophenol is prepared by reductively decomposing a bis(hydroxyphenyl)sulfides conventionally prepared by the method disclosed in U.S. Pat. No. 3,647,885 according to which phenol and elementary sulfur in admixture without any solvent are reacted at an elevated temperature in the presence of an alkali metal hydroxide as a catalyst. The product of this reaction is, of course, a mixture of various kinds of different bis(hydroxyphenyl)sulfides, from which the reductive decomposition gives a mixture of mercaptophenols containing the undesired 2-mercaptophenol in a large or major proportion so that this process is industrially not advantageous in respect of the productivity of 4-mercaptophenol.

An alternative method is disclosed in Japanese Patent Kokai No. 50-24233 for the preparation of bis(hydroxyphenyl)sulfides, according to which phenol and sulfur chloride are reacted in an organic solvent such as methyl alcohol, acetonitrile, 1,2-dimethoxy ethane, acetic acid and ethyl acetate. This method is, however, disadvantageous in respect of formation of chlorophenols as a by-product and low selectivity for the formation of the desired bis(hydroxyphenyl)sulfide. In addition, the reaction product obtained by this method contains a relatively large amount of monosulfides insusceptible to the reductive decomposition and, moreover, the reductive decomposition of the reaction product gives the desired 4-mercaptophenol in a relatively low yield with a large amount of undesired 2-mercaptophenol as a by-product.

SUMMARY OF THE INVENTION

The present invention accordingly has an object to provide an improved method for the preparation of a mixture of bis(hydroxyphenyl)sulfides, from which the reductive decomposition gives 4-mercaptophenol in a greatly increased proportion relative to 2-mercaptophenol, by the reaction of phenol and sulfur chloride.

Thus, the method of the present invention for the preparation of a bis(hydroxyphenyl)disulfide comprises reaction phenol and sulfur chloride in a solvent which is an ethylene glycol monoalkyl ether compound represented by the general formula $$R\text{-}(OCH_2\text{-}CH_2)_n\text{-}OH, \quad (I)$$

in which R is an alkyl group having 1 to 6 carbon atoms and the subscript n is a positive integer not exceeding 5.

DETAILED DESCRIPTION OF THE PREFERRED EMBODIMENTS

The above summarized method of the invention is characterized by the use of a specific ethylene glycol monoalkyl ether compound as the solvent for the reaction of phenol and sulfur chloride. This method has been established on the base of the discovery that the selectivity of the reaction between phenol and sulfur chloride is greatly influenced by the type of the solvent and that the best result can be obtained unexpectedly by the use of the above mentioned specific solvent in which a mixture of bis(hydroxyphenyl)sulfides capable of being reductively decomposed to 4-mercaptophenol is obtained in such a high purity that the product of the reductive decomposition can be used in the synthesis of 1,7-di(4-hydroxyphenylthio)-3,5-dioxaheptane without further purification.

The reaction of phenol and sulfur chloride is expressed by the following reaction equation assuming that the product is a disulfide:

$$2C_6H_5OH + S_2Cl_2 \rightarrow HO.C_6H_4\text{-}S\text{-}S\text{-}C_6H_4.OH + 2HCl.$$

The sulfureous reactant in the inventive method is sulfur chloride or, more precisely, disulfur dichloride, of the formula $S_2Cl_2$ which can be used either as a solid or in the form of vapor. This particular sulfur compound can react with phenol even without using any catalyst to form a mixture bis(hydroxyphenyl)sulfides.

The reaction of phenol and sulfur chloride in the inventive method is performed in an organic solvent which is an ethylene glycol monoalkyl ether compound represented by the above given general formula (I). In the formula, R is an alkyl group having 1 to 6 carbon atoms or, preferably, 1 to 4 carbon atoms and the subscript n is a positive integer not exceeding 5 or, preferably, not exceeding 3.

The ethylene glycol monoalkyl ether compound suitable for use as a solvent in the inventive method accordingly includes ethylene glycol monoalkyl ethers, diethylene glycol monoalkyl ethers, triethylene glycol monoalkyl ethers, tetraethylene glycol monoalkyl ethers and pentaethylene glycol monoalkyl ethers. The alkyl group in these monoalkyl ethers may be selected from the class consisting of methyl group, ethyl group, n-propyl group, isopropyl group, n-butyl group, isobutyl group, tert-butyl group, pentyl groups and hexyl groups.

In practicing the inventive method, sulfur chloride is used in an amount in the range from 0.25 to 2 moles or, preferably, from 0.4 to 1 mole per mole of phenol. When the amount of sulfur chloride is too small, conversion of phenol into bis(hydroxyphenyl)disulfide is decreased. When the amount of sulfur chloride is too large, on the other hand, the reaction product may contain an increased amount of by-products. The solvent, in which the reaction is performed, is used in an amount, usually, in the range from 40 to 2000 ml or, preferably, from 80 to 1000 ml per mole of phenol. When the amount of the solvent is too small, the reductive decomposition of the reaction product of the bis(- hydroxyphenyl)sulfide gives an increased amount of 2-mercaptophenol relative to the desired 4-mercaptophenol. Increase of the amount of the solvent over the above mentioned upper limit has no particular additional advantages rather with some economical disadvantages.

In a preferred procedure for practicing the inventive method, phenol and the solvent are introduced into a reaction vessel and phenol is completely dissolved in the solvent by agitating the mixture under an atmosphere of an inert gas such as nitrogen followed by the addition of liquid sulfur chloride dropwise into the mixture in the vessel kept at a controlled temperature. The reaction temperature is in the range from $-50°$ C. to $+100°$ C. or, preferably, $-30°$ C. to $+70°$ C. The reaction can proceed satisfactorily under normal pressure although it is optional to conduct the reaction under reduced pressure or under increased pressure according to need. The reaction is completely usually within 0.1 to 10 hours.

By performing the reaction of phenol and sulfur chloride in a specific solvent according to the inventive method described above, bis(hydroxyphenyl)sulfides can be prepared with high selectivity, from which 4-mercaptophenol is obtained by the reductive decomposition reaction in such a high purity that the product of the reductive decomposition can be used as such in the synthetic preparation of 1,7-di(4-hydroxyphenylthio)-3,5-dioxaheptane useful as a color developing agent in heat-sensitive recording paper.

In the following, the method of the invention is described in more detail by way of examples.

EXAMPLES 1 TO 5 AND COMPARATIVE EXAMPLES 1 TO 5

Into a three-necked flask of 50 ml capacity equipped with an electromagnetic stirrer, thermometer, Dimroth condenser, inlet tube for nitrogen gas and rubber cap to serve as a membrane seal for thrusting an injection needle were taken 20 m moles of phenol and 10 ml of an organic solvent indicated below and the mixture was agitated at room temperature under a stream of nitrogen gas until a uniform solution was obtained.

Solvent used.
Example 1: ethylene glycol monomethyl ether
Example 2: ethylene glycol monoethyl ether
Example 3: ethylene glycol mono(n-butyl)ether
Example 4: diethylene glycol monoethyl ether
Example 5: triethylene glycol monoethyl ether
Comparative Example 1: methyl alcohol
Comparative Example 2: acetonitrile
Comparative Example 3: 1,2-dimethoxy ethane
Comparative Example 4: acetic acid
Comparative Example 5: ethyl acetate Then, the temperature of the reaction mixture in the flask was controlled at a temperature indicated in the table as the "temperature for $S_2Cl_2$ addition" by dipping the flask in a water bath, if necessary, with addition of ice. Thereafter, 11 m moles of liquid sulfur chloride taken in a syringe of injector were introduced dropwise into the reaction mixture kept at the "temperature for $S_2Cl_2$ addition" under the nitrogen atmosphere through the injection needle thrusted into the rubber cap over a period of 15 minutes followed by further continued agitation of the mixture kept at the "reaction temperature" indicated in the table for the "reaction time" also indicated in the table.

After the end of the reaction time, 40 ml of water were added to the reaction mixture and the mixture was tested for acidity followed by three times of extraction each with 50 ml of diethyl ether. The ether extracts combined together were washed three times each with 50 ml of water and then subjected to stripping of the solvent to leave an oily material as the product. This product was subjected to a gas chromatographic analysis and high-performance liquid chromatographic analysis for the identification of the sulfide compounds and determination of the conversion of phenol and selectivity of the reaction into the monosulfide and di- and trisulfides as well as small amounts of higher sulfides as combined based on the phenol converted into the sulfide compounds. The results are shown in the table which also shows the yield of the chlorophenols in %.

In the next place, the above obtained oily product was transferred into an Erlenmeyer flask of 100 ml capacity and dissolved by adding 10 ml of toluene. The solution was then admixed with 16 m moles of zinc dust and heated at 50° C. Thereafter, 4.5 ml of concentrated hydrochloric acid were added dropwise into the reaction mixture kept at 50° C. in the flask under agitation over a period of 5 minutes followed by further continued agitation for additional 60 minutes to effect the reductive decomposition of the sulfides with disappearance of the zinc dust in the mixture. The mixture in the flask was then transferred to a separatory funnel and washed three times each with 30 ml of water followed by evaporation of the solvent to leave a second oily material as the product. This oily product was subjected to a gas chromatographic analysis for the identification of the species in the product mainly composed of mercaptophenols and determination of the conversion of the sulfide compounds and selectivity of the reaction between 4- and 2-mercaptophenols on the base of the sulfides. The results are shown in the table.

TABLE 1

|  |  | Example | | | | | Comparative Example | | | | |
|---|---|---|---|---|---|---|---|---|---|---|---|
|  |  | 1 | 2 | 3 | 4 | 5 | 1 | 2 | 3 | 4 | 5 |
| Temperature of $S_2Cl_2$ addition, °C. | | 2–5 | 16–20 | 2–5 | 12–15 | 12–15 | 16–20 | 12–15 | 16–20 | 12–15 | 2–5 |
| Reaction temperature, °C. | | 3 | 50 | 3 | 15 | 15 | 50 | 15 | 50 | 15 | 3 |
| Reaction time, hours | | 2 | 0.5 | 2 | 1 | 1 | 0.5 | 1 | 0.5 | 1 | 2 |
| Conversion of phenol, % | | 86 | 95 | 94 | 96 | 98 | 45 | 99 | 97 | 79 | 90 |
| Selectivity of sulfides, % by moles | monosulfide | 1 | 1 | 6 | 5 | 4 | 0 | 25 | 4 | 6 | 6 |
| | di-, tri- & higher sulfides | 99 | 99 | 94 | 95 | 96 | 100 | 75 | 91 | 83 | 86 |
| Yield of chlorophenols, % | | 0 | 0 | 0 | 0 | 0 | 0 | 0 | 5 | 11 | 8 |
| Conversion of sulfides, % | | 99 | 99 | 94 | 95 | 96 | 100 | 75 | 91 | 83 | 86 |
| Selectivity of mercaptophenols, | 4 mercaptophenol | 98 | 98 | 99 | 98 | 98 | 90 | 96 | 94 | 88 | 92 |
| | 2-mercapto- | 2 | 2 | 1 | 2 | 2 | 10 | 4 | 6 | 12 | 8 |

What is claimed is:

1. A method for the preparation of a bis(hydroxyphenyl)sulfide mixture which comprises reacting phenol and $S_2Cl_2$ in a solvent which is an ethylene glycol monoalkyl ether compound represented by the general formula $$R \text{---} (OCH_2\text{---}CH_2)_n\text{---}OH,$$

in which R is an alkyl group having 1 to 6 carbon atoms and the subscript n is a positive integer not exceeding 5.

2. The method for the preparation of a bis(hydroxyphenyl)sulfide mixture as claimed in claim 1 wherein the alkyl group denoted by R has 1 to 4 carbon atoms.

3. The method for the preparation of a bis(hydroxyphenyl)sulfide mixture as claimed in claim 1 wherein the subscript n is a positive integer not exceeding 3.

4. The method for the preparation of a bis(hydroxyphenyl)sulfide mixture as claimed in claim 1 wherein the amount of sulfur chloride is in the range from 0.25 to 2 moles per mole of phenol.

5. The method for the preparation of a bis(hydroxyphenyl)sulfide mixture as claimed in claim 1 wherein the amount of the solvent is in the range from 40 to 2000 ml per mole of phenol.

6. The method for the preparation of a bis(hydroxyphenyl)sulfide mixture as claimed in claims 1, 2, 3, 4, or 5 wherein the reaction is performed at a temperature in the range from $-50°$ C. to $+100°$ C.

7. The method for the preparation of a bis(hydroxyphenyl)sulfide mixture as claimed in claims 1, 2, 3, 4 or 5 wherein the reaction is performed in an inert atmosphere.

8. The method for the preparation of a bis(hydroxyphenyl)sulfide mixture as claimed in claims 1, 2, 3, 4 or 5 wherein the reaction is performed in an inert atmosphere at a temperature in the range from $-50°$ C. to $+100°$ C.